United States Patent
Pack et al.

(10) Patent No.: US 9,120,464 B2
(45) Date of Patent: Sep. 1, 2015

(54) SENSOR SYSTEM IN A MOTOR VEHICLE

(75) Inventors: Andreas Pack, Hagenau (FR); Axel Schwarz, Baden-Baden (DE); Bruno Hodapp, Achern-Oensbach (DE); Norbert Hog, Appenweier (DE); Henry Blitzke, Buehl (DE)

(73) Assignee: ROBERT BOSCH GMBH, Stuttgart (DE)

( * ) Notice: Subject to any disclaimer, the term of this patent is extended or adjusted under 35 U.S.C. 154(b) by 1125 days.

(21) Appl. No.: 13/091,339

(22) Filed: Apr. 21, 2011

(65) Prior Publication Data
US 2011/0267624 A1    Nov. 3, 2011

(30) Foreign Application Priority Data
Apr. 29, 2010    (DE) .......................... 10 2010 028 347

(51) Int. Cl.
*G01N 21/47*    (2006.01)
*B60S 1/08*    (2006.01)

(52) U.S. Cl.
CPC ..... *B60S 1/0837* (2013.01); *G01N 2201/06126* (2013.01)

(58) Field of Classification Search
CPC . G01N 21/47; G01N 21/4738; G01N 21/474; G01N 21/55; G01N 21/552; G01N 2201/0626; G01N 2201/0634; G01N 2201/06126; B60S 1/0833; B60S 1/0837; B60S 1/0844; B60S 1/0811; B60S 1/0888; B60S 1/0822; B60S 1/0877
USPC ........... 250/573, 574, 221, 222.1, 216, 559.4, 250/338.5, 338.1, 341.8, 341.1; 356/445, 356/446; 73/170.17, 170.21; 362/503
See application file for complete search history.

(56) References Cited

U.S. PATENT DOCUMENTS

| | | | |
|---|---|---|---|
| 3,947,131 A * | 3/1976 | Karl .............................. 356/445 |
| 4,652,745 A * | 3/1987 | Zanardelli ................ 250/227.25 |
| 4,701,613 A * | 10/1987 | Watanabe et al. ............ 340/602 |
| 4,859,867 A * | 8/1989 | Larson et al. ................ 307/10.1 |
| 4,867,561 A * | 9/1989 | Fujii et al. .................. 356/239.8 |
| 4,871,917 A * | 10/1989 | O'Farrell et al. .......... 250/341.7 |
| 4,973,844 A * | 11/1990 | O'Farrell et al. .......... 250/341.7 |
| 5,661,303 A * | 8/1997 | Teder .......................... 250/341.8 |
| 5,898,183 A * | 4/1999 | Teder ............................ 250/574 |
| 5,998,782 A * | 12/1999 | Koyama et al. .......... 250/227.25 |

(Continued)

FOREIGN PATENT DOCUMENTS

| CN | 1306175 | 8/2001 |
|---|---|---|
| CN | 201100967 | 8/2008 |

(Continued)

*Primary Examiner* — John Lee
(74) *Attorney, Agent, or Firm* — Kenyon & Kenyon LLP

(57) ABSTRACT

A sensor system is described for detecting wetting of a window includes a photodetector having multiple light-sensitive elements and a light source for emitting light to a detection region of the window in such a way that a portion of the light is reflected at the window, and another portion of the light passes through the window. The light source and the light-sensitive element are situated in such a way that a portion of the light from the light source which passes through the window is reflected at the wetting and strikes a portion of the light-sensitive elements. The light source includes a lighting element which is set up to irradiate into a transparent body. The transparent body has a surface which has defined unevennesses for the diffuse radiation of the irradiated light.

20 Claims, 4 Drawing Sheets

(56) References Cited

U.S. PATENT DOCUMENTS

| | | | |
|---|---|---|---|
| 6,084,519 A * | 7/2000 | Coulling et al. | 340/602 |
| 6,232,603 B1 * | 5/2001 | Nelson | 250/339.11 |
| 6,307,198 B1 * | 10/2001 | Asakura et al. | 250/227.25 |
| 6,376,824 B1 * | 4/2002 | Michenfelder et al. | 250/214 R |
| 6,404,490 B2 * | 6/2002 | Blasing | 356/239.8 |
| 6,573,490 B2 * | 6/2003 | Hochstein | 250/227.25 |
| 6,768,099 B1 * | 7/2004 | Cheng et al. | 250/227.24 |
| 7,259,367 B2 | 8/2007 | Reime | |
| 7,414,237 B2 * | 8/2008 | Richwin et al. | 250/227.25 |
| 7,429,745 B2 * | 9/2008 | Yoshigoe et al. | 250/573 |
| 7,468,523 B2 * | 12/2008 | Ishikawa | 250/573 |
| 7,492,459 B2 * | 2/2009 | Takata et al. | 356/445 |
| 7,573,576 B2 * | 8/2009 | Mordau et al. | 356/445 |
| 7,718,943 B2 * | 5/2010 | Johnson et al. | 250/208.1 |
| 7,894,054 B2 * | 2/2011 | Backes | 356/239.8 |
| 8,082,783 B2 * | 12/2011 | Backes | 73/170.17 |
| 8,269,202 B2 * | 9/2012 | Backes | 250/573 |
| 2002/0190231 A1 * | 12/2002 | Kobayashi et al. | 250/573 |
| 2006/0076478 A1 * | 4/2006 | Johnson et al. | 250/227.25 |
| 2006/0163458 A1 | 7/2006 | Reime | |
| 2007/0235638 A1 * | 10/2007 | Backes et al. | 250/227.24 |
| 2007/0268585 A1 * | 11/2007 | Santoro et al. | 359/599 |
| 2008/0116379 A1 * | 5/2008 | Teder | 250/341.1 |
| 2008/0297803 A1 * | 12/2008 | Backes | 356/445 |
| 2009/0261237 A1 * | 10/2009 | Backes | 250/227.11 |
| 2011/0267624 A1 * | 11/2011 | Pack et al. | 356/446 |

FOREIGN PATENT DOCUMENTS

| | | |
|---|---|---|
| DE | 10 2004 015 040 | 10/2005 |
| DE | 10 2007 003 023 | 7/2008 |

* cited by examiner

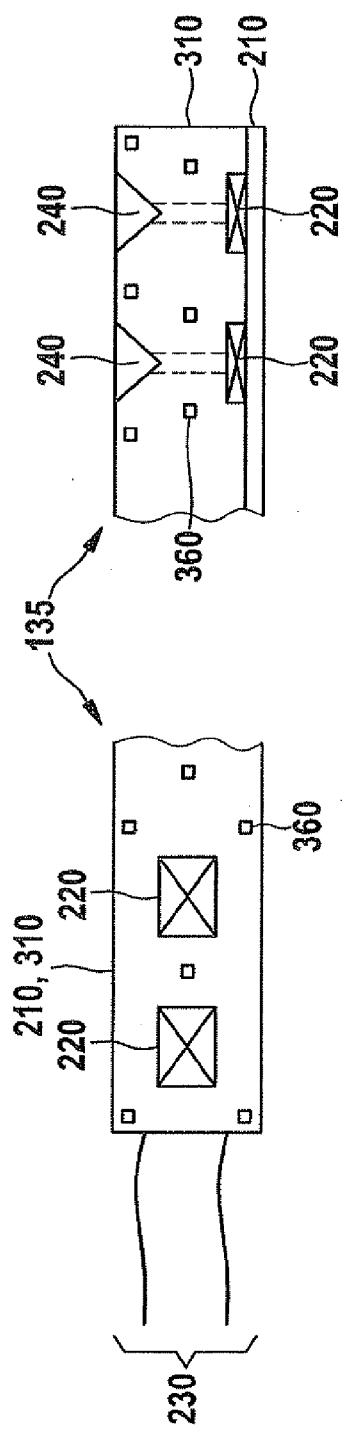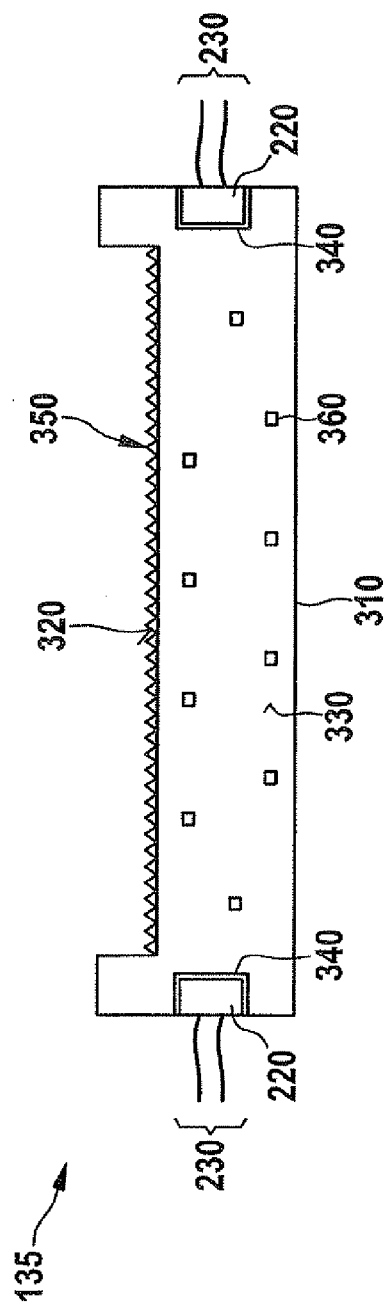

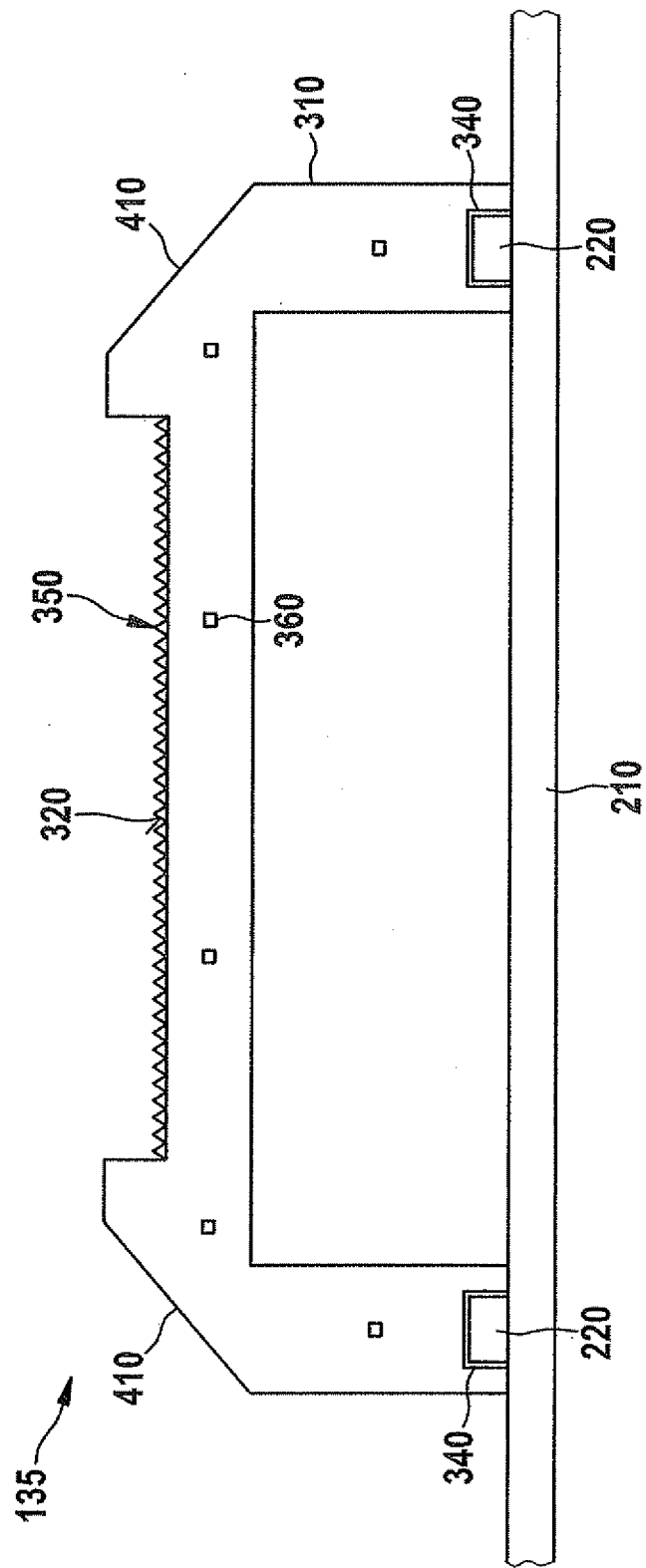

SENSOR SYSTEM IN A MOTOR VEHICLE

RELATED APPLICATION INFORMATION

The present application claims priority to and the benefit of German patent application no. 10 2010 028 347.9, which was filed in Germany on Apr. 29, 2010, the disclosure of which is incorporated herein by reference.

FIELD OF THE INVENTION

The present invention relates to a sensor system in a motor vehicle.

BACKGROUND INFORMATION

To keep a window of a motor vehicle free from visual obstructions, various devices are known which guide a window wiper over the window whenever visual obstructions which may be cleaned off are present. Such automatically activated window wiper systems are advantageous in particular when the wetting of the window with water drops varies in intensity as the result of variable precipitation, for example.

In one variant of a system for determining the wetting, light from a light source is injected into the window in such a way that the light is cast back and forth in total reflection between the inner and outer surfaces of the window. If wetting, for example in the form of a water drop, is present in the region of these total reflections, the reflection is disturbed and a portion of the light exits from the window pane. A light sensor that registers light which originates from the light source and which is totally reflected at another location at the window is able to register such a loss of light, and a signal may thus be provided which is a function of wetting of the window.

U.S. Pat. No. 7,259,367 B2 discloses a sensor system in which water drops on the window are determined based on a comparison of camera data of a window, with and without illumination by a controlled light source.

DE 10 2004 015 040 A1 discloses a sensor system based on the principle of total reflection, using a camera, the camera supplying image data for a driver assistance system, and a portion of an image sensor surface in the camera being reserved for determining raindrops on the window.

A sensor system which is based on irradiating the inner surface of the window in such a way that a small portion of the light may be reflected at the surface of the window, while a large portion of the light may pass through the window, and the light is reflected on a water drop and is cast into a photodetector, places high demands on the light source used. The light irradiated for illuminating the window should be as homogeneous as possible so that the detection quality is not made a function of a location of the water drop. Lastly, the entire sensor system should be manufactured as cost-effectively as possible and should be easy to install. For this purpose, the light source should have a high degree of efficiency so that a major portion of energy supplied to the light source is converted into light, and the generated light should strike a predetermined sensitive surface of the window. A high intensity of the light striking the window is advantageous.

SUMMARY OF THE INVENTION

An object of the exemplary embodiments and/or exemplary methods of the present invention is to provide an improved sensor system according to these specifications.

This object may be achieved by a sensor system having the features according to the description herein. Specific embodiments are also described herein.

According to the exemplary embodiments and/or exemplary methods of the present invention, a sensor system for detecting wetting of a window includes a photodetector having multiple light-sensitive elements and a light source for emitting light to a detection region of the window in such a way that a portion of the light is reflected at the window, and another portion of the light passes through the window. The portion of the light reflected by the window should be as small as possible, and the portion of the light passing through the window should be as large as possible. The light source and the light-sensitive element are situated in such a way that a portion of the light from the light source which passes through the window is reflected by the wetting and strikes a portion of the light-sensitive elements. The light source includes one or multiple lighting elements which are set up to irradiate into a transparent body, the transparent body having a surface which has defined unevennesses for the diffuse radiation of the irradiated light. A graphical image of the wetting may be recorded and processed in the photodetector with the aid of the information recorded by the multiple light-sensitive elements.

A light source for diffuse light may thus be easily and cost-effectively manufactured, allowing suitable illumination of the detection region of the window.

The lighting element may irradiate into the transparent body in any desired direction, which may be in a direction that is essentially perpendicular to the radiation direction. In this way good diffusion of the irradiated light may be provided, and at the same time ease of installation of the lighting element on the transparent body may be increased.

The light source may include a further lighting element, the lighting elements irradiating into the transparent body in different directions. Thus, luminance of the lighting element may be increased while maintaining good homogeneity of the radiated diffuse light. Ease of installing the lighting element on the transparent body may be maintained. The transparent body may have an outer surface for the total reflection of irradiated light in a direction perpendicular to the radiation direction. Thus, the transparent body of the sensor system may at the same time carry out the function of a light guide, so that a position of the radiating surface with respect to the lighting element(s) may be flexibly provided.

In one specific embodiment, the unevennesses are microlenses. In this way an exit direction of the light may be influenced in a targeted manner; in addition, a luminous efficiency may be increased.

In one alternative specific embodiment, the unevennesses are defined by a roughness. The roughness may be introduced into the surface as parallel or nondirectional furrows with the aid of an abrasive wheel, for example. In another specific embodiment, the roughness may be produced via the molding process for the light guide, for example by an appropriate design of an injection molding tool. The roughness allows a good diffusion action with low manufacturing costs.

An outer surface of the transparent body may be mirrored. Light which is irradiated by the lighting element into the transparent body and which does not directly strike the surface having the defined unevennesses may be reflected at the mirrored outer surface until the light exits through the uneven surface. Efficiency of the lighting element may be further increased by this cost-effective measure. Alternatively, for this purpose a reflection at an unmirrored surface via total reflection may take place.

The transparent body may have a recess for accommodating the lighting element, so that the lighting element is encased by the transparent body. Thus, the portion of the light exiting from the lighting element which is used for the light source may be increased.

Scattering particles may be provided in the light guide in order to diffusely distribute the irradiated light. A directionality of the irradiated light may thus be eliminated or diminished, and the exiting light may have a more uniform distribution. Optionally, the scattering bodies may cause the light to be deflected from the irradiation direction into the exit direction.

The lighting element may include a light-emitting diode. In this way the light source may advantageously be easily adapted to a specified light wavelength and may be manufactured in a cost-effective manner. In the case of multiple light-emitting diodes, a nonuniform luminous efficiency of multiple light-emitting diodes may be compensated for as a result of the good scattering effect of the transparent body having the defined uneven surface. The light emitted by the lighting element may have a wavelength that is invisible to the human eye, for example infrared light in the wavelength range greater than 780 nm, in particular between 780 nm and 1400 nm. Visual distractions which may be perceived by persons in the range of the sensor system may thus be avoided. This applies in particular to a driver of a motor vehicle in which the sensor system is installed.

A mirror may be provided on which the diffusely radiated light falls, the mirror having a design which is integrated with the transparent body. Manufacturing tolerances in positioning the mirror with respect to the light source may be reduced in this way.

The exemplary embodiments and/or exemplary methods of the present invention are described in greater detail with reference to the appended figures.

BRIEF DESCRIPTION OF THE DRAWINGS

FIG. 2 shows a specific embodiment of a light source for the sensor system from FIG. 1.

FIG. 3 shows another specific embodiment of a light source for the sensor system from FIG. 1.

FIG. 4 shows another specific embodiment of a light source for the sensor system from FIG. 1.

DETAILED DESCRIPTION

Figure 1:
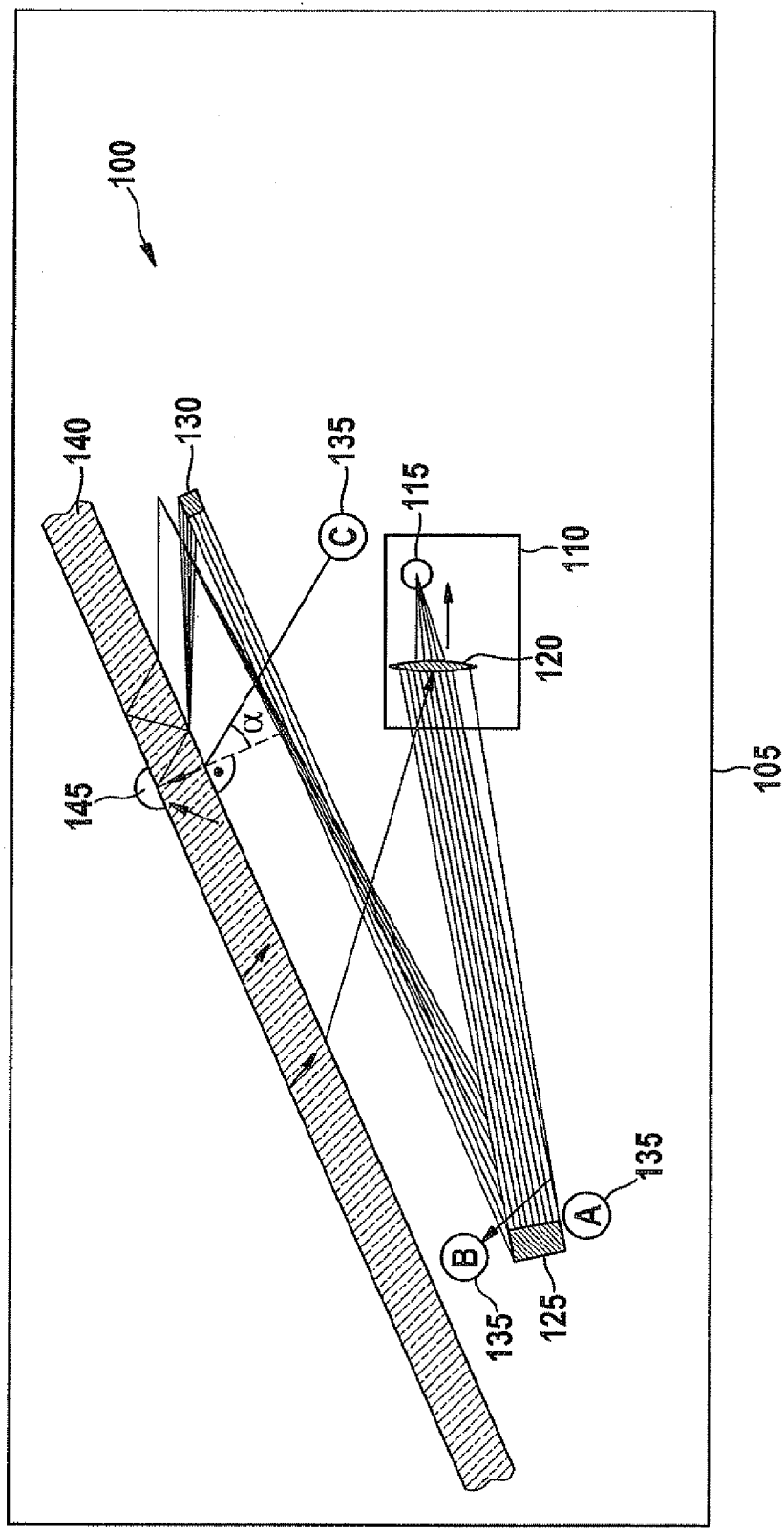
FIG. 1 shows a sensor system onboard a motor vehicle.

FIG. 1 shows a sensor system 100 onboard a motor vehicle 105. Sensor system 100 includes a camera 110 having a two-dimensional digital image sensor 115 for scanning an image, and having a lens 120. A group of optical elements may be used instead of lens 120 in order to improve imaging properties. Sensor system 100 also includes a first mirror 125, and a light source 135 which is illustrated in three different positions A, B, and C as examples. Sensor system 100 is situated in the region of a window pane 140 of motor vehicle 105 in order to detect the presence of a drop 145 wetting window pane 140.

Camera 110 is mounted in motor vehicle 105 in such a way that a field of vision of camera 110 through window pane 140 is situated outside motor vehicle 105, window pane 140 may be a windshield, and camera 110 recording an image from the surroundings of motor vehicle 105. The image provided by camera 110 may be supplied to a driver assistance system such as a lane departure warning system or a parking assistance system, or may also be evaluated by another system of motor vehicle 105, for example a rear view camera. A focus range of camera 110 is set, with the aid of lens 120, to a range outside motor vehicle 105, which may be close to infinite.

To be able to also image raindrop 145 distinctly enough in the image provided by camera 110, the beam path between drop 145 and camera 110 is extended with the aid of mirrors 125 and 130.

As a result of the geometric configuration of sensor system 100, the image of drop 145 on sensor 115 on camera 110 may be completely superimposed on the image recorded from the surroundings of motor vehicle 105, or may be limited to a portion of the image in camera 110. To be able to also detect a small drop 145 and to detect spatial and/or temporal distributions of drops 145 on window pane 140, the largest possible region of the image in camera 110 may be used for detecting raindrop 145.

Raindrop 145 may be optically imaged in a range of sensor 115 of camera 110 in two different ways. On the one hand, light from the surroundings of motor vehicle 105 may strike drop 145 and be deflected via mirrors 125 and 130 into camera 110 and onto image sensor 115.

To allow reliable recognition of drop 145 under difficult light conditions, for example essential absence of light, intense solar radiation at a low angle of incidence, or rapidly changing light conditions, on the other hand drop 145 may be illuminated from the inside of window pane 140 with the aid of light source 135. Light which strikes drop 145 in this way is reflected at one of the boundary surfaces delimiting drop 145, and enters camera 110 via mirrors 125 and 130, similarly as described above. The reflective boundary surface may be situated between drop 145 and window pane 140, or between drop 145 and the air cushions surrounding same.

Light source 135 is advantageously situated in such a way that light irradiated by the light source does not directly enter camera 110. A diaphragm, a screening, or a silvering (not shown) may optionally be used to preclude a direct beam path from light source 135 into camera 110. In general, a light beam from light source 135 strikes the inside of window pane 140 at an acute angle, thus undergoing partial reflection (Fresnel reflection). A portion of the light beam is reflected at the surface of window pane 140, while another portion of the light beam is admitted by window pane 140. The ratio of the reflected portion to the admitted (transmitted) portion of the light beam is a function of the size of the angle of incidence and the optical densities of air and of window pane 140.

In order to maximize a portion of the light beam which is admitted by window pane 140, it is generally advantageous to minimize an angle of incidence $\alpha$ on window pane 140 of the light beam emanating from light source 135. In customary notation, the angle of incidence is measured relative to the perpendicular to the boundary surface. Position C of light source 135 meets this requirement.

On the other hand, a large angle of incidence $\alpha$ causes a larger portion of the light from light source 135 which strikes drop 145 to be reflected at its boundary surface, so that ultimately more light from raindrop 145 enters camera 110, thus allowing more reliable detection. This may be achieved when light source 135 is in position B. On the other hand, positioning of light source 135 at position B may result in shading of a region of the image of the surroundings of motor vehicle 105 in camera 110. Position A of light source 135 represents a satisfactory compromise.

FIG. 2 shows light source 135 of sensor system 100 from FIG. 1. FIG. 2a shows a top view, and FIG. 2b shows a side view. Multiple light-emitting diodes 220 are situated in a row on a printed circuit board 210. Light-emitting diodes 220 may be conventional or surface-mounted components (surface mounted devices (SMD)), and may operate in an invisible light spectrum, for example infrared, in order to avoid visual irritation to a person inside or outside motor vehicle 105. Light-emitting diodes 220 are connected to one another, and may be activated via connections 230. The light outputs and/or radiation angles of light-emitting diodes 220 may vary due to manufacturing tolerances, so that without further measures, uniform illumination in sensor system 100 from FIG. 1 is not ensured. The quality of detection of raindrop 145 on window pane 140 may thus be a function of a position of drop 145 on window pane 140. Individual activation of light-emitting diodes 220 or calibration of light-emitting diodes 220 is complicated and expensive.

To ensure a homogeneous luminous flux, transparent body 210 therefore has depressions 240 in its surface in the region of the exiting light. The depressions may have a conical design, as shown, and may be situated above light-emitting diodes 220. The light which is radiated by light-emitting diodes 220 is reflected in lateral directions at the boundary surfaces of depressions 240. Additionally or alternatively, the surface of transparent body 210 may be rough in order to cause scattering of the light. Surfaces of depressions 240 may likewise be rough. In another specific embodiment the surfaces may also be mirrored. In addition, scattering particles 360, explained in greater detail below with reference to FIG. 3, may be provided in transparent body 210.

FIG. 3 shows an improved light source 135 of sensor system 100 from FIG. 1 in a side view. In a transparent body 310, light-emitting diodes 220 irradiate laterally from the right and left sides. Connections 230 of light-emitting diodes 220 lead away to the right and left, but may also be connected to one another so that they interconnect light-emitting diodes 220. Transparent body 310 may be made, for example, of a thermoplastic plastic such as acrylic glass or polycarbonate, for example Makrolon.

Transparent body 310 has a rough surface 320 with unevennesses 350. In the illustration in FIG. 3, light source 135 radiates upwardly. Surface 320 extends perpendicularly to the radiation direction of light source 135, in the horizontal direction.

Light-emitting diodes 220 are accommodated in recesses 340 corresponding thereto in transparent body 310. Light irradiated from light-emitting diodes 220 into transparent body 310 is completely or partially reflected at surfaces of transparent body 310, provided that the angle of incidence is large enough. Due to the roughness of surface 320, there is a relatively high probability that the angle of incidence in this region is small enough for light to exit, so that diffuse light exits upwardly from surface 320.

The roughness of surface 320 provides a good distribution of the exiting light, thus producing a sufficiently homogenous luminous flux. Unevennesses 350 on surface 320 may be, for example, microlenses, microprisms, or other periodic surface elements. In another specific embodiment, a desired roughness may be provided in a cost-effective manner via parallel or nondirectional furrows which are introduced into transparent body 310 with the aid of a scribing element or an abrasive wheel, for example. The roughness may also be achieved by an appropriate roughness of an injection molding tool in which transparent body 310 is produced.

To keep losses due to reflections at other surfaces of transparent body 314 as low as possible so that light irradiated by light-emitting diodes 220 into transparent body 310 does not exit via any other surface than rough surface 320, the other surfaces may be mirrored, such as mirrored surface 330, for example. Light may be prevented from exiting toward the observer in relation to FIG. 3 with the aid of mirrored surface 330.

In addition, optional scattering bodies 360 are provided which diffusely distribute the light which is irradiated by light-emitting diode 220. Scattering particles 360 have reflective surfaces or have a different index of refraction than transparent body 310, which allows them to form a so-called volume hologram.

FIG. 4 shows another specific embodiment of light source 135 of sensor system 100 from FIG. 1, in a side view. Transparent body 310 is stretched in a bridge or U shape between two light-emitting diodes 220 which are situated on printed circuit board 210. Light-emitting diodes 220 irradiate into transparent body 210 essentially upwardly, the emitted light being reflected to a great extent in a horizontal direction at angled surfaces 410. An upper region of illustrated light source 135 corresponds to the illustration from FIG. 3, in that the light deflected by angled surfaces 410 extends horizontally in transparent body 310 and is diffusely radiated upwardly via rough surface 320.

Angled surfaces 410, the same as surfaces 330 from FIG. 3, may be mirrored. As a result of the bridged design of transparent body 310, space may be provided on printed circuit board 210, beneath transparent body 310, for additional components, for example for activating light-emitting diodes 220. In addition, installation of transparent body 310 is simplified by mounting on printed circuit board 210 which is already fitted with light-emitting diodes 220.

Figure 5:
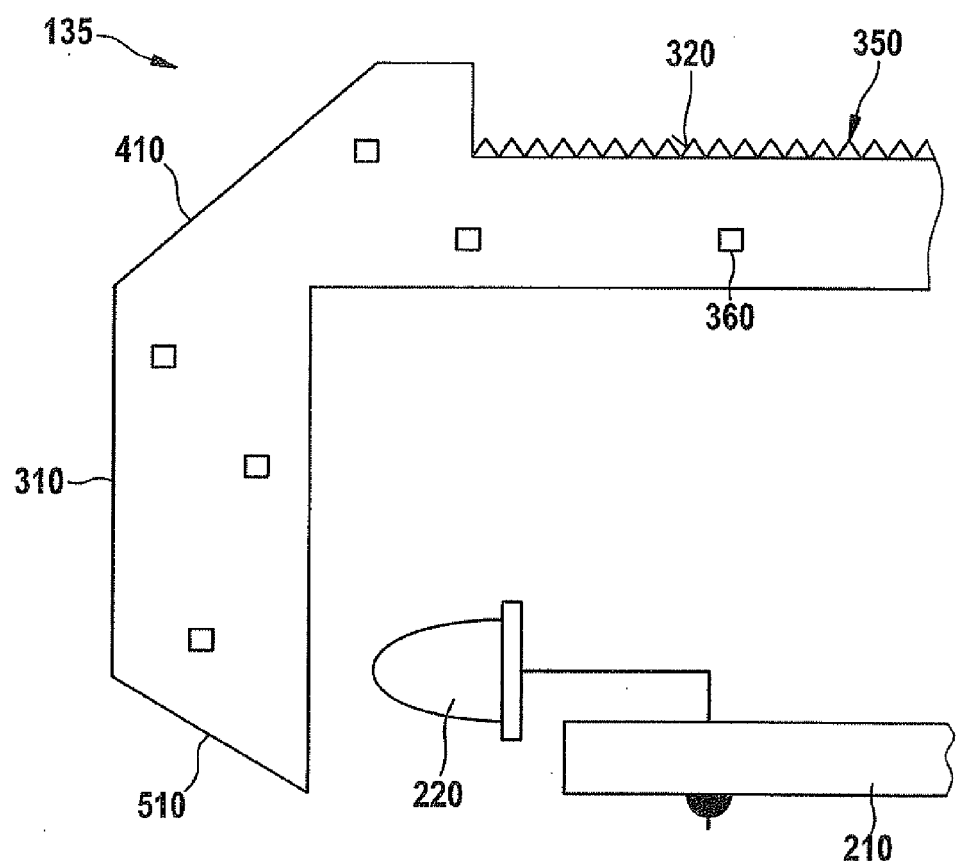
FIG. 5 shows another specific embodiment of a light source for the sensor system from FIG. 1.

FIG. 5 shows a detail of light source 135 from FIG. 4 in an alternative specific embodiment in a side view. In contrast to the specific embodiment illustrated in FIG. 4, light-emitting diode 220 irradiates into transparent body 310 in the horizontal direction, the major portion of the light being deflected upwardly, in the direction of angled surface 410, at a further angled surface 510. The further beam path is achieved as described above with reference to FIG. 4.

What is claimed is:

1. A sensor system for detecting a wetting of a window, comprising:
    a photodetector having multiple light-sensitive elements; and
    a light source for emitting light to the window so that a portion of the light is reflected at the window, and another portion of the light passes through the window, the light source including:
        a transparent body having a surface which has defined unevenness, and
        a lighting element which is set up to irradiate into the transparent body in a direction that is substantially perpendicular to a radiation direction of the light source,
        wherein the defined unevenness is for diffuse radiation of the irradiated light;
    wherein the light source and the photodetector are situated so that a portion of the light from the light source which passes through the window is reflected at the wetting and strikes a portion of the multiple light-sensitive elements.

2. The sensor system of claim 1, wherein the light source includes a further lighting element, the lighting elements irradiating into the transparent body in different directions.

3. The sensor system of claim 1, wherein the transparent body has an outer surface for the total reflection of irradiated light in a direction perpendicular to the radiation direction.

4. The sensor system of claim 1, wherein the defined unevenness is at least one microlens.

5. The sensor system of claim 1, wherein the unevenness is defined by a roughness.

6. The sensor system of claim 5, wherein the roughness is introduced to the surface which has defined unevenness as parallel or nondirectional furrows.

7. The sensor system of claim 1, wherein an outer surface of the transparent body is mirrored.

8. The sensor system of claim 1, wherein the transparent body has a recess for accommodating the lighting element, so that the lighting element is encased by the transparent body.

9. The sensor system of claim 1, wherein the lighting element includes a light-emitting diode.

10. The sensor system of claim 1, wherein the light emitted by the lighting element has a wavelength that is invisible to the human eye.

11. The sensor system of claim 10, wherein the wavelength of the light emitted by the lighting element is in a range of 780 nm to 1400 nm.

12. The sensor system of claim 1, wherein the diffusely radiated light falls on a mirror, the mirror being integrated with the transparent body.

13. The sensor system of claim 1, wherein the transparent body is also a light guide.

14. The sensor system of claim 13, wherein scattering particles are provided in the light guide to diffusely distribute the irradiated light.

15. The sensor system of claim 14, wherein the scattering particles cause light to be deflected from the direction of irradiation from the lighting element into an exit direction.

16. The sensor system of claim 1, wherein the transparent body has depressions in a surface in a region proximal to where light is irradiated from the lighting element.

17. The sensor system of claim 1, wherein the transparent body is a thermoplastic plastic.

18. The sensor system of claim 1, wherein the transparent body is stretched in one of a bridge shape or a U shape between two light-emitting diodes.

19. A sensor system for detecting a wetting of a window of a motor vehicle, comprising:
   a camera having a two-dimensional digital image sensor and a lens, the digital image sensor for scanning an image;
   a first mirror; and
   a light source for emitting light to the window so that a portion of the light is reflected at the window, and another portion of the light passes through the window, the light source including:
      a transparent body having a surface which has defined unevenness, and
      a lighting element which is set up to irradiate into the transparent body in a direction that is substantially perpendicular to a radiation direction of the light source,
      wherein the defined unevenness is for diffuse radiation of the irradiated light;
   wherein the light source and the camera are situated so that a portion of the light from the light source which passes through the window is reflected at the wetting and strikes the digital image sensor.

20. The sensor system of claim 19, wherein the light source is situated so that light emitted by the light source does not directly enter the camera.

* * * * *